(12) United States Patent
Bertrand et al.

(10) Patent No.: US 7,856,987 B2
(45) Date of Patent: Dec. 28, 2010

(54) ELECTRONIC VALVE READER

(75) Inventors: William J. Bertrand, Ventrua, CA (US);
Lori C. Speckman, Ventura, CA (US);
Robert N. Golden, Kirkland, WA (US);
Gary Sanders, Kirkland, WA (US);
Steve Vincent, Kirkland, WA (US);
Daniel R Morris, Renton, WA (US)

(73) Assignee: Medtronic, Inc., Minneapolis, MN (US)

( * ) Notice: Subject to any disclaimer, the term of this patent is extended or adjusted under 35 U.S.C. 154(b) by 522 days.

(21) Appl. No.: 12/037,228

(22) Filed: Feb. 26, 2008

(65) Prior Publication Data

US 2008/0221436 A1    Sep. 11, 2008

Related U.S. Application Data

(63) Continuation of application No. 10/698,095, filed on Oct. 31, 2003, now Pat. No. 7,334,582.

(51) Int. Cl.
*A61B 19/00* (2006.01)
(52) U.S. Cl. .................................................. 128/899
(58) Field of Classification Search ............... 600/9–15; 128/897–899; 324/207.11, 207.26, 228, 324/231, 326, 329, 345, 347, 348; 604/8–10, 604/247–248
See application file for complete search history.

(56) References Cited

U.S. PATENT DOCUMENTS

| 4,676,772 | A  | * | 6/1987 | Hooven | 604/9 |
| 6,216,028 | B1 | * | 4/2001 | Haynor et al. | 600/424 |
| 2002/0022793 | A1 | * | 2/2002 | Bertrand et al. | 604/9 |
| 2002/0077673 | A1 | * | 6/2002 | Penner et al. | 607/60 |
| 2003/0004403 | A1 | * | 1/2003 | Drinan et al. | 600/301 |

* cited by examiner

*Primary Examiner*—Samuel G Gilbert
(74) *Attorney, Agent, or Firm*—Dicke, Billig, & Czaja, PLLC (57) ABSTRACT

The invention is directed toward a magnetic valve reader used as an indicator tool. The magnetic valve reader determines a location and an orientation for a magnetic indicator device to indicate a device setting of an implantable medical device. The implantable medical device includes the magnetic indicator device coupled to a valve on the implantable medical device. External magnetic fields, specifically the Earth's magnetic field, may interfere with the compass and create an incorrect device setting indication. The electronic reader estimates the external magnetic fields to subtract the estimate from received data to minimize any influence that external magnetic field has on the accuracy of the device setting measurement.

21 Claims, 8 Drawing Sheets

ELECTRONIC VALVE READER

CROSS-REFERENCE TO RELATED APPLICATIONS

This application is a continuation of U.S. patent application Ser. No. 10/698,095, filed Oct. 31, 2003, and entitled "Electronic Valve Reader", which is now U.S. Pat. No. 7,334,582, issued Feb. 26, 2008; the entirety of which is incorporated herein by reference.

FIELD

The invention relates to medical devices and, more particularly, to magnetic reader-based indicator tools.

BACKGROUND

Magnetic-based indicator tools are used to determine a setting of an implantable medical device. The implantable medical device may include a fluid flow control valve that controls the pressure of cerebral spinal fluid (CSF) in a patient's brain. Excessive accumulation of cerebral spinal fluid (CSF), due to hydrocephalus or other causes, manifests itself as increased pressure within the brain. Relieving the CSF pressure is therapeutically beneficial and is usually done by using a fluid flow control valve to drain CSF from ventricles in the brain.

The implantable medical device may include a target in the form of a magnet. The magnet allows a tool set to determine the setting of the medical device and change the setting without removing the subcutaneously implanted device. The tool set typically includes a locator tool to determine the orientation of the medical device, the magnetic-based indicator tool to determine the setting of the implantable medical device by using a compass, and an adjustment tool to change the setting of the medical device by using another magnet. The tool set works by using magnetic coupling between the magnet on the implantable medical device and each of the indicator tool compass and the adjustment tool magnet.

The compass-based indicator tool relies on an interaction between the magnet on the medical device and the compass that is strong enough to determine the position of the magnet even through a patient's scalp. The magnet-compass interaction must also be resistant to external magnetic fields, especially from the Earth. The compass will drift toward aligning with the Earth's magnetic field if the pull of the magnet in the implanted medical device is not strong enough. The deflection angle increases as the distance between the magnet and the compass increases, and may lead to inaccurate device setting indications.

Alternatively, magnetic based location tools have been developed to determine the three-dimensional location and orientation of magnetic devices within implanted medical devices, such as medical tubes and catheters. These alternate location systems typically do not relate to the rotatable orientation of magnetic devices that are part of implantable valve devices.

U.S. Published Patent Application No. 2002/0022793 to Bertrand et al. discloses a compass-based indicator for assessing the position of a fluid flow valve within an implanted device. The fluid flow valve described by Bertrand et al. may be used for controlling the flow of cerebral spinal fluid (CSF) in a patient with hydrocephalus. This compass-based indicator is used in combination with an implantable flow control device disclosed within U.S. Pat. No. 5,637,083 to Bertrand et al. U.S. Pat. No. 5,879,297 and U.S. Pat. No. 6,129,668 to Haynor et al. discloses an electronic device to determine the location and orientation of a magnet coupled to an indwelling medical device using a plurality of magnetic sensors. Table 1 below lists documents that disclose devices for determining the location and orientation of magnetic devices within implantable medical devices.

TABLE 1

| Patent Number | Inventors | Title |
| --- | --- | --- |
| U.S. Pat. No. 5,637,083 | Bertrand et al. | Implantable Adjustable Fluid Flow Control Valve |
| 2002/0022793 | Bertrand | Tool for Adjusting an Implantable Adjustable Fluid Flow Control Valve |
| U.S. Pat. No. 5,879,297 | Haynor et al. | System and Method to Determine the Location and Orientation of an Indwelling Medical Device |
| U.S. Pat. No. 6,129,668 | Haynor et al. | System and Method to Determine the Location and Orientation of an Indwelling Medical Device |

All documents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the structures and techniques of the present invention.

SUMMARY

In general, the invention is directed to an electronic device for determining the location and orientation of magnets coupled to implantable medical devices. The electronic device is included in a magnetic-based indicator tool for interaction with an implanted medical device to assess a setting associated with the device. The invention has certain objects. That is, various embodiments of the present invention provide solutions to one or more problems existing in the prior art with respect to the magnetic-based indicator tools for interaction with implanted medical devices.

The problems include, for example, inaccuracies in the setting indication provided by a compass-based indicator tool due to the effects of external magnetic fields. The compass-based indicator tool interacts with a magnetic target that creates an internal magnetic field, and causes the compass to indicate a particular position. The position of the compass is indicative of the setting of the implantable medical device, e.g., the position of a fluid flow valve. External magnetic fields, and especially the Earth's magnetic field, may interfere with the compass and create an incorrect device setting indication.

Various embodiments of the present invention have the object of solving the foregoing problems. For example, it is an object of the present invention to overcome at least some of the disadvantages of the foregoing procedures by providing an electronic-based magnetic location and orientation based indicator tool that produces more accurate and reliable indications of implantable device settings. To that end, it is a further object of the present invention to reduce the effects of an external magnetic field on the electronic-based indicator tool, and thereby enhance the accuracy of the tool. It is another object of the invention to reduce the effects of an external magnetic field by electronically measuring and compensating for the presence of the external magnetic field. The invention is also capable of sensing the implanted magnet at a greater distance (such as in the case where there is thick skin or scalp tissue over the implanted device) than the prior compass-based tool. A third advantage is that the current invention is that it is much less sensitive to alignment with the implanted device. The compass based tool must be positioned within about 1 cm or less from coaxial with the implanted device to provide an accurate reading. With the current invention, the implanted device must only be encircled by the sensor array. Precise coaxial centering is not required.

Various embodiments of the invention may possess one or more features capable of fulfilling the above objects. In general, the invention is directed to an electronic magnetic-based indicator tool that includes a plurality of magnetic field sensors and a processing system that uses data generated from the plurality of magnetic field sensors to determine a location and orientation of a magnetic indication device. The magnetic indication device, being coupled to a valve used to control operation on an implantable flow control device, permits the processing module to further determine a setting for the valve from the location and orientation of the magnetic indication device.

In another embodiment, the invention is directed to a system comprising an implantable medical device that includes an implantable flow control device, an electronic magnetic-based indicator tool, and an adjustment tool. The implantable flow control device includes a magnetic device coupled to a control valve. The electronic magnetic-based indicator tool that includes a plurality of magnetic field sensors and a processing system that uses data generated from the plurality of magnetic field sensors to determine a location and orientation of a magnetic indication device. The magnetic device, being coupled to a valve used to control operation on an implantable flow control device, permits the processing module to further determine a setting for the valve from the location and orientation of the magnetic indication device.

In another embodiment, the invention is directed to a method which comprises placing a electronic magnetic-based indicator tool adjacent to an implantable medical device, detecting a magnet field from a plurality of magnetic field sensors, estimating a background magnet field from a sequence of magnetic field data observed over time, and indicating a device setting of the implantable medical device, wherein the device setting is indicated by the indicator tool. The plurality of target magnetic field sensors and the plurality of background magnetic field sensors are located a distance apart sufficient to permit the background magnetic field sensors to only detect ambient magnetic fields when the target magnetic field sensors are located near the implanted flow control device.

In comparison to known implementations of magnetic-based indicator tools for implantable medical devices, various embodiments of the present invention may provide one or more advantages. For example, if the implantable medical device is implanted subcutaneously on a patient's skull, an electronic magnetic-based indicator tool in accordance with the invention is capable of taking a more accurate device setting measurement through the patient's skin. As a magnetic-based indicator tool moves further away from the magnet contained within an implantable medical device, external magnetic fields have a relatively greater influence on the indicator tool. The magnetic sensors of the present invention enable estimation and compensation of the external magnetic fields and thus prevent the corruption of the device setting measurement, even as the distance increases between the indicator tool and the implantable medical device. The electronic indicator tool is then able to display accurate device setting values in the cases where the patient's skin is thicker than normal. In this way, the electronic indicator tool may eliminate the need for x-rays to determine an implantable medical device setting through a surface, such as a patient's skin.

It is a primary object of the present invention to provide an improvement to magnetic-based indicator tools for use with implantable medical devices. This and other objects of the invention will become clear from an inspection of the detailed description of the invention and from the appended claims. Throughout the description, like elements are referred to by like reference numbers. An element referred to by a reference number has all the attributes and characteristics of the element as described wherever in the description unless specifically stated otherwise.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION

Figure 1:
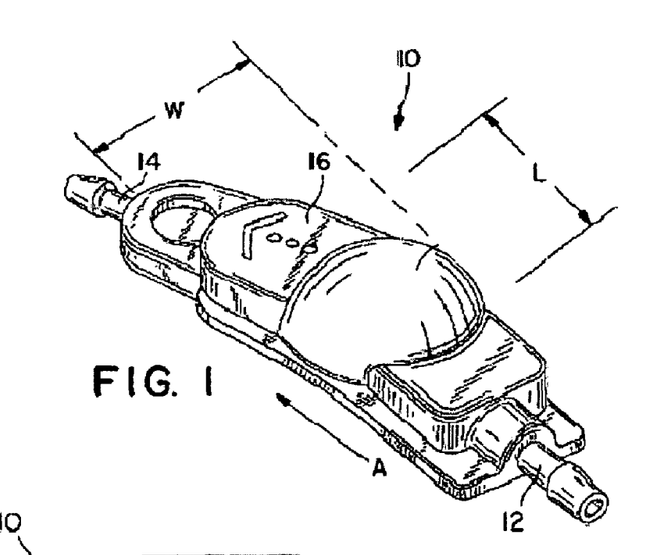
FIG. 1 is a schematic diagram illustrating a subcutaneously implantable and adjustable fluid flow control device for use with an improved valve reader device according to an example embodiment of the present invention.
Figure 2:
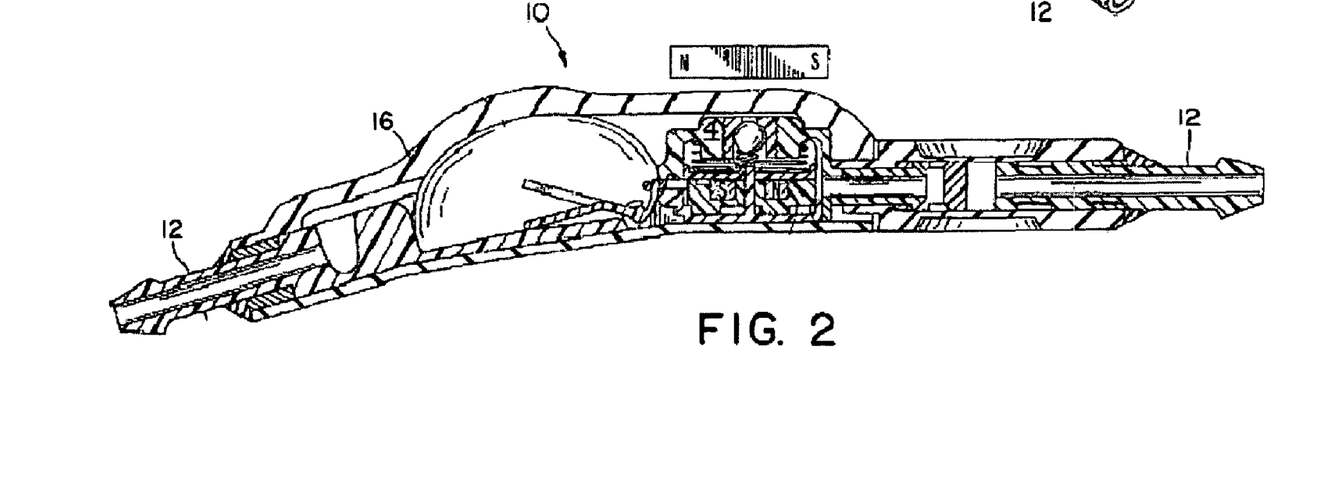
FIG. 2 is a cross-sectional diagram further illustrating the subcutaneously implantable and adjustable fluid flow control device of FIG. 1.

As shown in the drawings for purposes of illustration, the FIGS. 1 and 2 illustrate a subcutaneously implantable and percutaneously adjustable fluid flow control device, generally designated in the accompanying drawings by the reference numbers 10. The fluid flow control devices 10 is intended for use in a surgically implanted physiological shunt system for draining fluid from one portion of the body to another. In order to connect, for example, the device 10 in such a system, the device includes an inlet connector 12 and an outlet connector 14 which each receive one end of a piece of surgical tubing (not shown). The ends of the surgical tubing are placed over the connectors 12 and 14 and secured thereon by a single ligature just inside of an annular ridge formed near the end of each connector.

When the flow control device 10 is used in a drainage system intended for the treatment of hydrocephalus, the inlet connector 12 is fluidly connected with a proximal catheter that is inserted through the skull into a brain ventricle containing cerebrospinal fluid under pressure. The outlet connector 14 is fluidly connected to a distal catheter that serves to discharge cerebrospinal fluid to, for example, the atrium portion of a patient's heart. Ordinarily the flow control device 10 will be surgically implanted on the patient's skull with a flap of skin overlying the device. To facilitate holding the device in its desired position after implantation, a generally flexible mounting plate can be provided with one or more suture holes.

The highly reliable fluid flow control device has a single flow path there through and a valve mechanism which can be percutaneously adjusted when the device is subcutaneously implanted by the use of the valve adjuster and reader device of the present invention. The flow control device 10 include a relatively rigid, molded plastic base invested within an elastomeric casing 16 which, together, define a fluid flow path through the fluid flow control devices from the inlet connector 12 to the outlet connector 14. The valve housing includes a percutaneously adjustable valve mechanism that restricts the flow of fluid through the device 10. Coupled to the adjustable valve mechanism is a magnetic indication device that may be externally located using an indicator tool. The present invention provides an improved mechanism for determining the setting of the adjustable valve mechanism. The flow control device is described in more detail in U.S. Pat. No. 5,637,083 issued to Bertrand et al. entitled "Implantable Adjustable Fluid Flow Control Valve."

Figure 3:
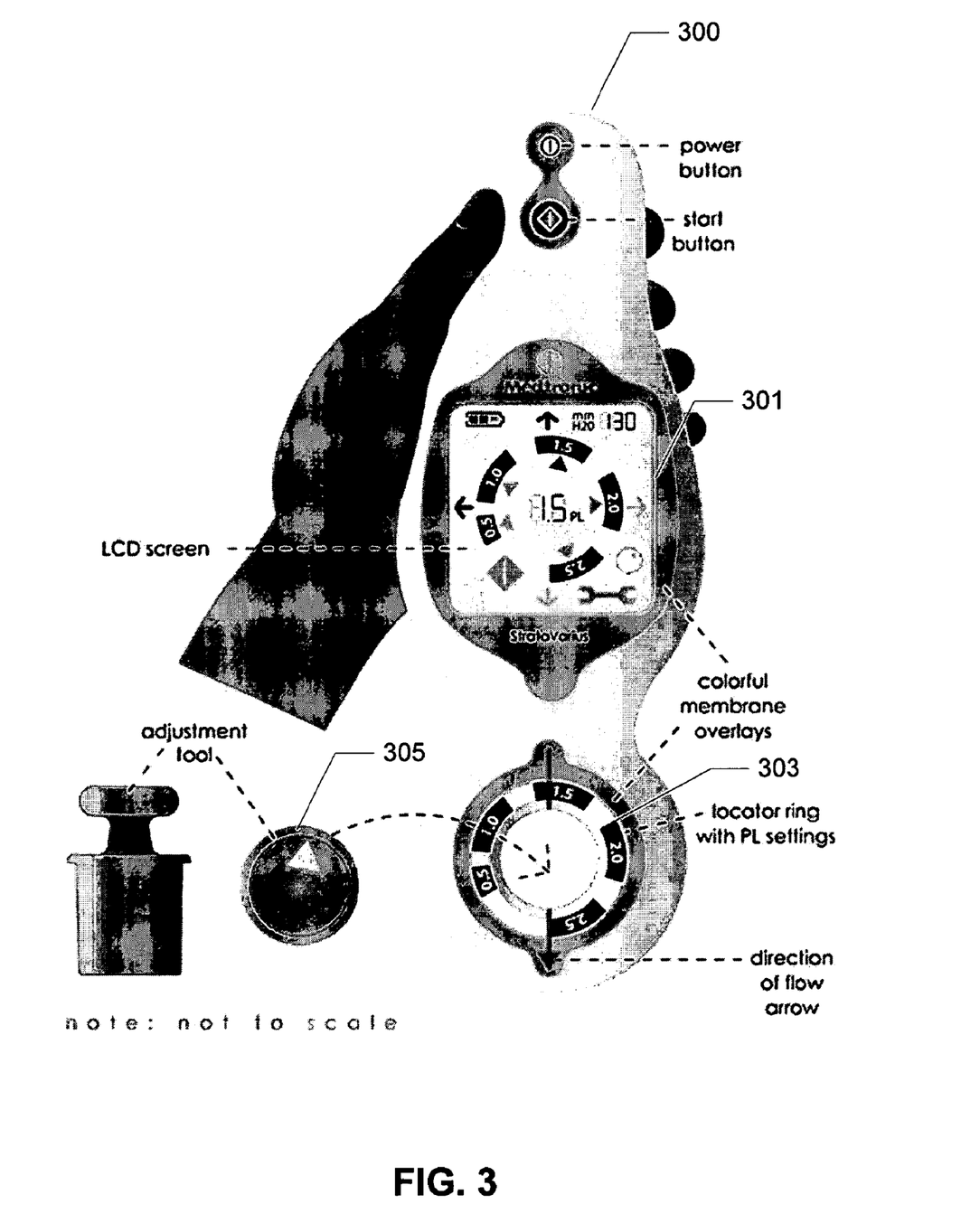
FIG. 3 is a diagram illustrating an improved electronic valve reader and adjustment tool in accordance with an example embodiment of the present invention.

FIG. 3 is a diagram illustrating an improved electronic valve reader and adjustment tool in accordance with an example embodiment of the present invention. The electronic valve reader 300 includes three main components: a valve reader sensor module 303, a display module 301, and an adjustment tool 305. The valve reader sensor module 303 corresponds to the sensor mechanism that electronically determines the location and orientation of a magnetic indication device that is an integral part of the implanted flow control device disclosed in the '083 patent. Valve reader sensor module 303 uses a plurality of magnetic sensor devices, as discussed below and as disclosed in detail in the '668 and the '297 patents identified above, to identify the location and orientation of the implanted magnetic device. Processing modules within the valve reader sensor module 303 determine a corresponding valve setting for the adjustable valve within the implanted flow control device based upon location and orientation of the magnetic indication device. In one embodiment, a valve reader sensor module 303 contains the magnetic field sensors and some associated support electronics, while processing, display, power supply circuitry, and batteries may be contained inside the rest of the unit 301.

From all of this information, the processing modules within the valve reader sensor modules 303 generate display data that is subsequently output to the display module 301 of the electronic valve reader 300. The display data represents a visual indication of the orientation of a valve control mechanism within the flow control device. The user of the reader may use this display data to determine whether the valve within the flow control device is set to a desired position.

In prior valve indicator devices, a magnetic compass has been used to determine an orientation for the magnetic indication device that is coupled to the valve control mechanism within the flow control device. This compass-based indication mechanism is replaced within the improved electronic valve reader with the electronic-based magnetic location and orientation processing system similar to the devices disclosed within the '668 and the '297 patents identified above. These prior patents locate a position and orientation of a magnetic device, such as a medical tube or catheter, but fail to indicate a valve orientation setting as a result of the determined orientation. The indicator mechanism of the present invention is less sensitive to environmental sources of magnetic fields that required prior indicator tools to be located extremely close to the flow control device in order to function properly.

When operating, the valve reader sensor module 303, and its plurality of magnetic sensor modules, are placed near the patient at a location in which the implanted flow control device is believed to be located. In many cases, a physician may accurately identify this location for the flow control device and the valve reader sensor module 303 may be located on top of the implanted flow control device. The electronics in the valve reader sensor module 303 process detected signals corresponding to magnetic fields generated by the magnetic indication device that is part of the flow control device. These electronic signals may also correspond to magnetic fields associated with ambient and environmental sources. The effects from these ambient and environmental sources may be subtracted from the detected signals to determine a more accurate indication for the location and orientation of the magnetic indication device that is part of the flow control device. The magnetic field data from each of the plurality of magnetic sensor modules permits a determination of the location and orientation of a magnetic indication device to be expressed in five degrees of freedom: x, y, z, pitch, and yaw.

From this determined orientation of the magnetic indication device that is part of the flow control device and from the known orientation of the flow control device, the processing modules may determine the present setting for the valve within the flow control device. The processing required to translate the position of the magnetic indication device to the setting of the valve within the flow control device is easily determined in that the value corresponds to a rotatable wheel having a position within a circle of rotation for the magnetic indication device that directly corresponds to the setting of the valve within the flow control device. This translation processing is well understood and disclosed in detail within the '668 and '297 patents as the orientation of a compass within its circle of rotation directly corresponded to the setting for the valve within the flow control device. Once the current position of the valve is determined and displayed, the adjustment tool 305 may be used to alter the setting for the valve within the flow control device.

Figure 4:
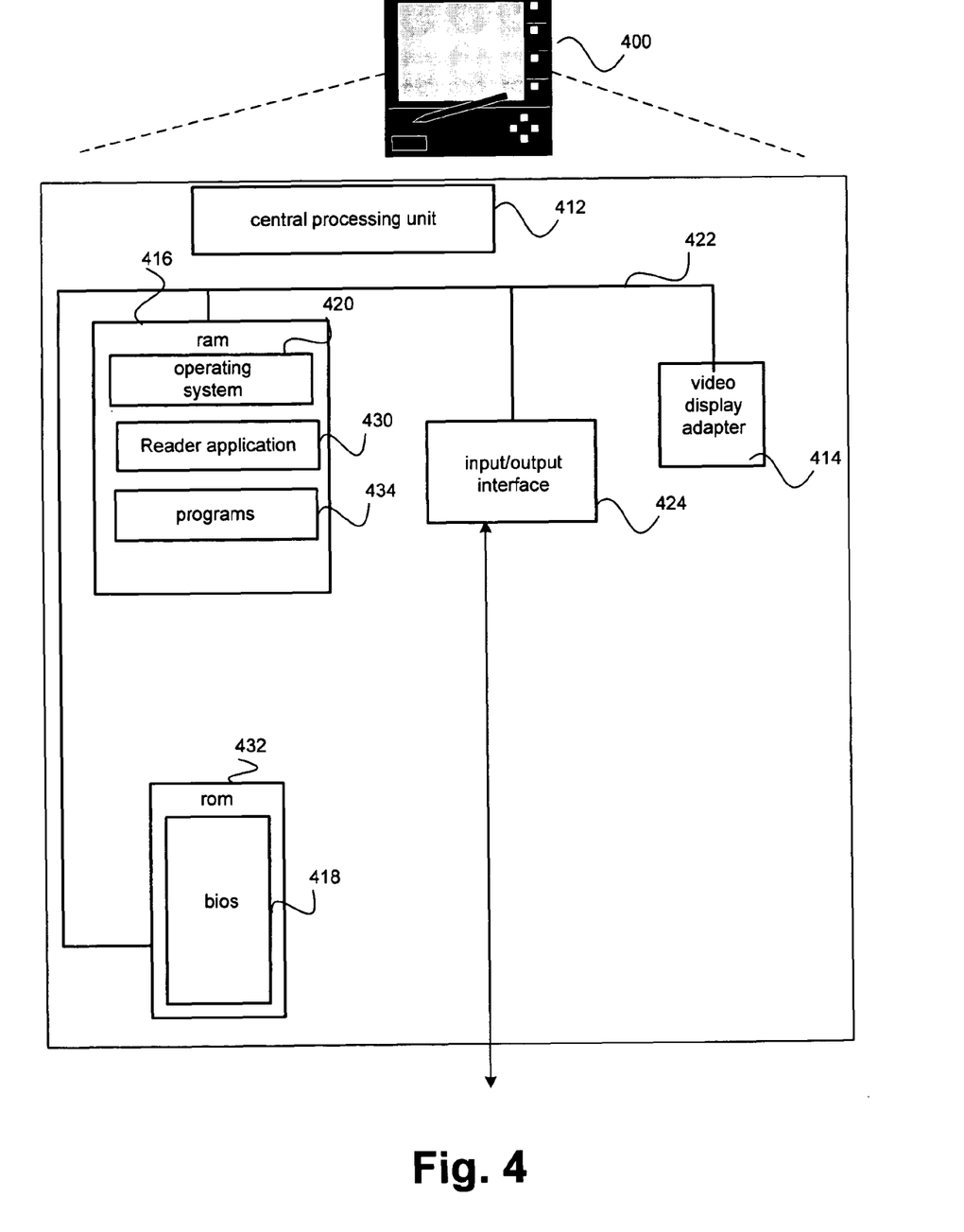
FIG. 4 is a block diagram illustrating a general programmable processing system for use in a handheld device such as an improved electronic valve reader and adjustment tool in accordance with an example embodiment of the present invention.

FIG. 4 is a block diagram illustrating a general programmable processing system for use in a handheld device such as an improved electronic valve reader and adjustment tool in accordance with an example embodiment of the present invention. In an exemplary embodiment of a handheld processing system 400, computing system 400 is operative to provide a magnetic valve reader processing system. Those of ordinary skill in the art will appreciate that the magnetic valve reader 400 may include many more components than those shown with reference to a computing system 400 shown in FIG. 4. However, the components shown are sufficient to disclose an illustrative embodiment for practicing the present invention.

As shown in FIG. 4, magnetic valve reader processing system 400 is used in connection with an implantable flow control device 10 as needed. The magnetic valve reader processing system 400 also includes processing unit 412, video display adapter 414, and a mass memory, all connected via bus 422. The mass memory generally includes RAM 416, ROM 432, and may include one or more mass storage devices, such as a removable memory device such as a Compact Flash, Smart Media, or Secure Digital memory card. The memory devices may store an operating system 420 for controlling the operation of magnetic valve reader processing system 400. It will be appreciated that this component may comprise a general purpose server operating system as is known to those of ordinary skill in the art, such as UNIX, MAC OS™, LINUX™, or Microsoft WINDOWS®. Basic input/output system ("BIOS") 418 is also provided for controlling the low-level operation of processing system 400.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. The mass memory also stores program code and data for providing a magnetic valve reader processing program. More specifically, the mass memory stores applications including magnetic valve reader program 430, and other programs 434, and similar analysis tool applications 436 as may be needed. The magnetic valve reader processing program 430 includes computer executable instructions which are executed to perform the logic described herein.

The magnetic valve reader processing system 400 also comprises input/output interface 424 for communicating with external devices, such as a touch screen and similar input devices, or other input devices not shown in FIG. 4. Likewise, the magnetic valve reader processing system 400 may further comprise additional mass storage facilities also not shown should additional data storage be needed.

One skilled in the art will recognize that the processing system illustrated within FIG. 4 may represent a set of processing components typically found within a handheld or similar dedicated processing system. Of course, other processing systems including general purpose computing systems containing additional peripherals and user interface devices may also be used to implement the programmable processing according to various embodiments of the present invention without deviating from the spirit and scope of the present invention as recited within the attached claims.

FIG. 4 illustrates an example of a suitable operating environment in which the invention may be implemented. The operating environment is only one example of a suitable operating environment and is not intended to suggest any limitation as to the scope of use or functionality of the invention. Other well known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. For example, a dedicated processing system may consist of a digital signal processor (DSP) for performing the required floating-point math, various internal memory types including FLASH, ROM, RAM, and FPGA, some minimal external memory for the valve calibration system, and a user interface and display driver chip to run the switches and custom LCD display. A proprietary embedded operating system is and a specifically written application for implementing the reader program may be included.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Processing devices typically include at least some form of computer readable media. Computer readable media can be any available media that can be accessed by these devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by processing devices.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Additionally, the embodiments described herein are implemented as logical operations performed by a programmable processing devices. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

Figure 5:
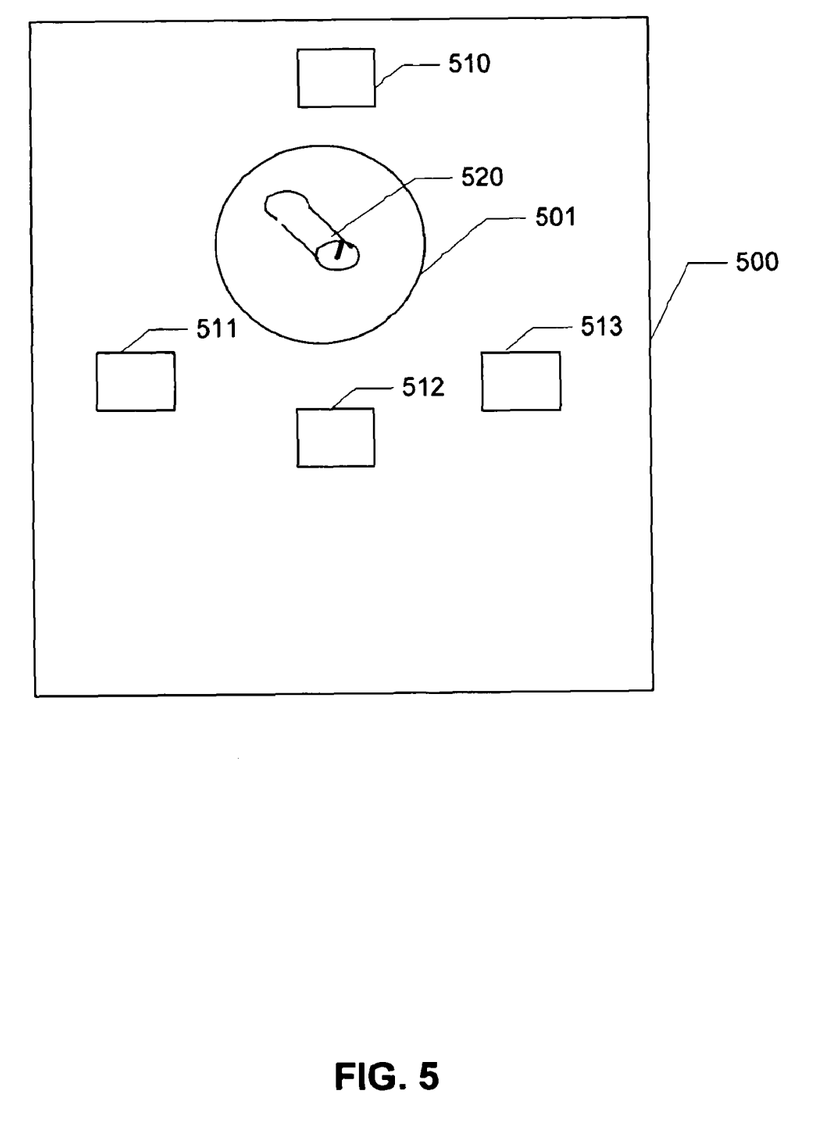
FIG. 5 is a block diagram illustrating a display showing a magnetic device within an improved electronic valve reader and adjustment tool in accordance with an example embodiment of the present invention.

FIG. 5 is a block diagram illustrating a magnetic device within an improved electronic valve reader and adjustment tool in accordance with an example embodiment of the present invention. The electronic valve reader 500 includes an opening 501 within the reader 500 that permits the reader 500 to be positioned over an implanted flow control device. The reader also includes a plurality of magnetic sensor devices 510-513 that each detect the magnetic field at their respective locations within reader 500. The magnetic field detected by each sensor 510-513 at its location is due to both background environmental magnetic fields and that arising from a magnetic device 520 located within the opening 501. As such, signals from the various magnetic sensor devices 510-513 may be processed to determine a location and orientation of the magnetic device 520 relative to the known positions of the magnetic sensor devices 510-513.

When the magnetic device 520 that is detected by the plurality of magnetic sensors corresponds to a magnetic indication device that is part of the valve within a flow control device, it is desired to determine the orientation of the magnetic indication device relative to a known position of the flow control device in order to accurately determine the setting for the valve within the flow control device. In one embodiment, the user orients the electronic valve reader to a known orientation relative to the implanted flow control device. As such, the orientation of the magnetic indication device, and thus the valve, is determined relative to this known orientation. Prior indicator tools that utilize a compass-based indicator required users to orient the tools relative to the flow control device to perform this identical determination. In other embodiments, additional measurements for additional position references may be used to perform this orientation and position translation operation. Because processing within the reader 500 may be updated periodically, and may occur several times per second, ambient and environmental sources of magnetic fields may be estimated and subtracted from the observed signals generated by the plurality of magnetic sensor devices 510-513. These magnetic sensor devices 510-513 are generally located at dispersed locations about the reader. In one embodiment, these sensors 510-513 may be located about one of the respective four corners of the reader. Use of these sensors in this fashion permits the reader device to sense implanted magnetic devices at greater distances while being less sensitive to being centered coaxially over the implanted flow control device as compared to compass-based devices.

Figure 6:
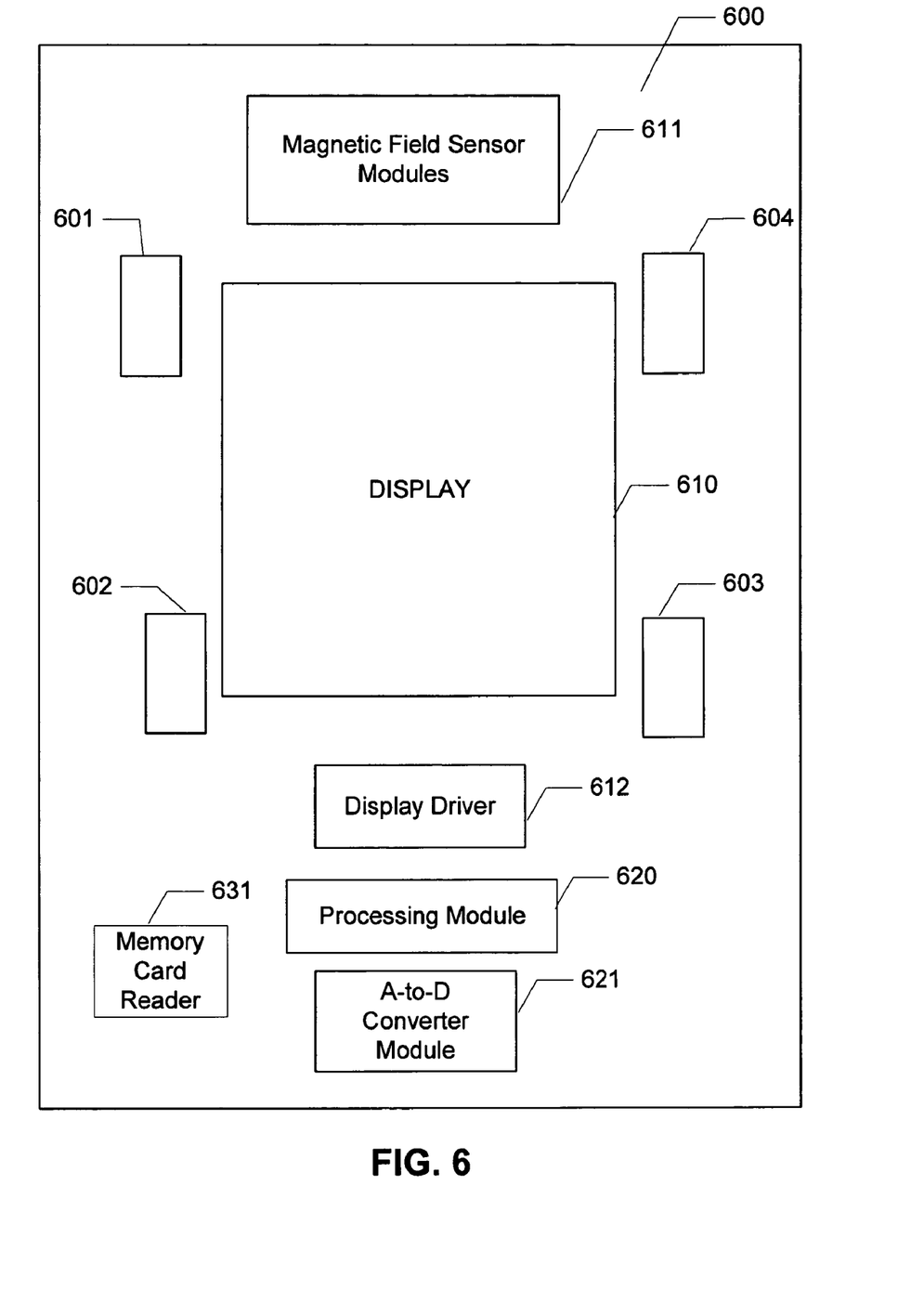
FIG. 6 is a block diagram illustrating a set of processing modules within an improved electronic valve reader and adjustment tool in accordance with another example embodiment of the present invention.

FIG. 6 is a block diagram illustrating a set of processing modules within an improved electronic valve reader and adjustment tool in accordance with another example embodiment of the present invention. The electronic valve reader 600 is constructed using a display module 610 that is surrounded by a plurality of magnetic field sensor modules 601-604. Each of these four sets of magnetic field sensors 601-604 contain three separate sensors so as to measure the full, three-dimensional vector magnetic field detected by the module at its location. The reader 600 also contains an analog-to digital converter module 621 and a combined magnetic field sensor module 611 to electronically process the signals generated by the magnetic field sensor modules 601-604 to obtain digital measurements corresponding the observed magnetic field.

These digital measurements of the observed magnetic field are subsequently processed within a processing module 620 to determine the location and orientation of a magnetic device within a field of view for the reader 600. The processing module corresponds to a programmable processing system as discussed above with respect to FIG. 4. The processing module performs operations upon the measured magnetic field data to determine the magnetic field generated by the magnetic device while subtracting an estimate for ambient and environmental magnetic field also observed by the magnetic field sensors 601-604. The processing performed in this determination of the location and orientation of the magnetic indication device is described in more detail within the '668 and the '397 patents to Haynor et al. discussed above.

From the above location and orientation of the magnetic device relative to the implantable flow control device, the processing module further determines the setting of the valve. This setting data is then used to generate a display image to be presented to a user on the display module 610. The processing module 620 outputs the display data to the display module 610 through a display driver 612.

The device may further contain a memory card reader 631 for accepting computer readable storage media. In one embodiment, this storage media may include compact flash, start media, secure digital, and memory stick memory cards for providing the device replaceable memory containing data usable by the device. For example, an implantable flow control device may permit fluid to flow at a particular pressure setting that corresponds to a particular setting on the valve. When the reader determines the valve setting, the data from the memory card may be used to display the corresponding pressure setting. Because the valve-to-pressure setting may vary from particular models of implantable flow control devices, the use or a memory card corresponding to the model of the flow control device will permit the reader device to easily display pressure values for a wide variety of flow control devices without needing to maintain all of the valve to pressure setting data for all devices at one time.

Figure 7:
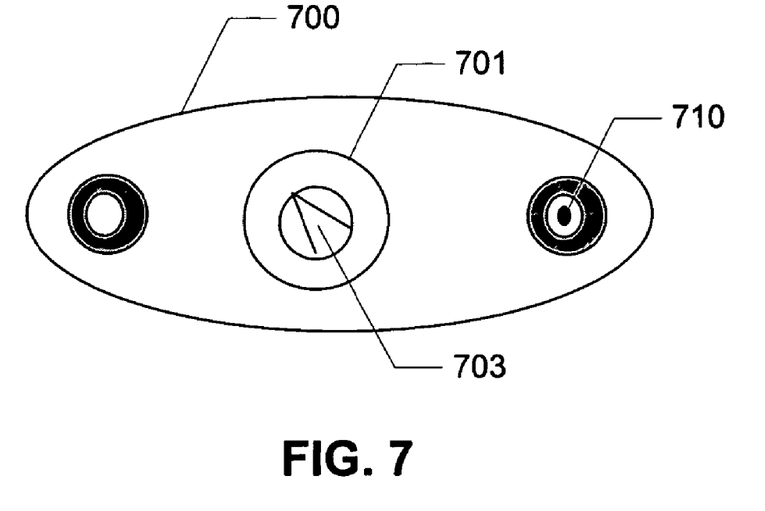
FIGS. 7 and 8 illustrate improved implantable valve devices possessing additional magnetic devices for used with an improved electronic valve reader and adjustment tool in accordance with an example embodiment of the present invention.
Figure 8:
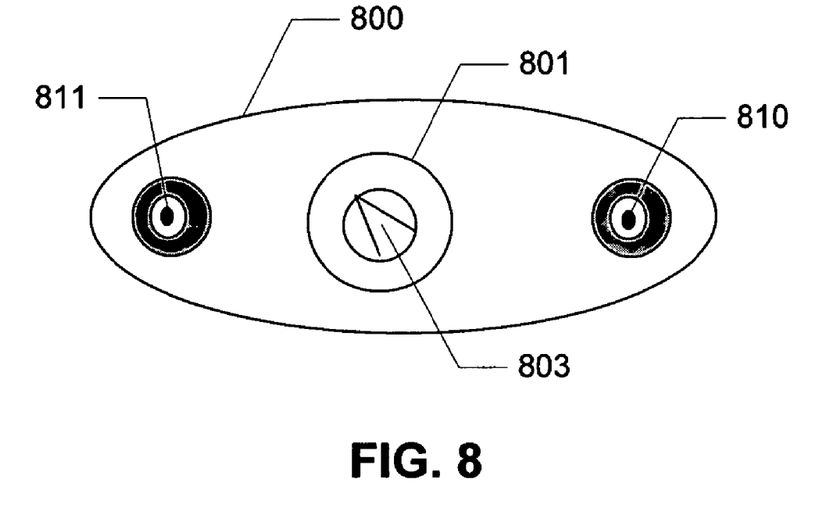

FIGS. 7 and 8 illustrate improved implantable valve devices possessing additional magnetic devices for used with an improved electronic valve reader and adjustment tool in accordance with an example embodiment of the present invention. As discussed above, the location and orientation of a detected magnetic device that is coupled to an implantable flow control device is used relative to an estimated position of the flow control device to determine the valve setting. This estimate is made because the valve is set by positioning the magnetic device coupled to the valve such that as the valve rotates about a known circular position, the magnetic field of the magnetic device also rotates about the same circle. In existing indicator tools, the tools must be aligned manually by a user into an orientation aligned with the implanted flow control device. This alignment process is also used in one embodiment of the electronic valve reader as discussed above.

In an alternate embodiment, an additional magnet 710 is coupled to the implantable flow control device 700 in a location separate from the valve 701 and its magnetic indicator device 703. The electronic reader, using the same processing to detect the magnetic device as discussed above, detects the location and orientation of the additional magnet 710. The location of the additional magnet 710 provides a reference point for the processing modules within the electronic valve reader to expressly determine the orientation of the electronic valve reader. The reader does not require the implanted flow control device to be position into a known orientation relative to the reader in order to accurately determine the setting of the valve. In this alternate embodiment, the setting of the valve may be made by determining the orientation of the magnetic device 703 coupled to the valve 701 relative to the position of the additional reference magnet 710. Using this method, the setting of the valve may be made accurately, yet independently of the orientation of the reader to the implanted flow control device.

In yet another embodiment, two separate reference magnets 810-811 are added to the valve 801 so that the orientation of the valve 801 and its corresponding magnetic indicator device 803 independently of the position of the reader. This second embodiment also works with separate embodiment of the reader. In alternate embodiment for the reader, the reader may utilize less magnetic sensors. The sensors would provide information regarding the general orientation of the detected magnetic fields. When the user orients the reader in this embodiment into a desired orientation aligned with the implanted flow control device, the setting of the valve 801 may be determined from the orientation of the magnetic fields observed from the magnetic indicator device 803 coupled to the valve 801.

Figure 9:
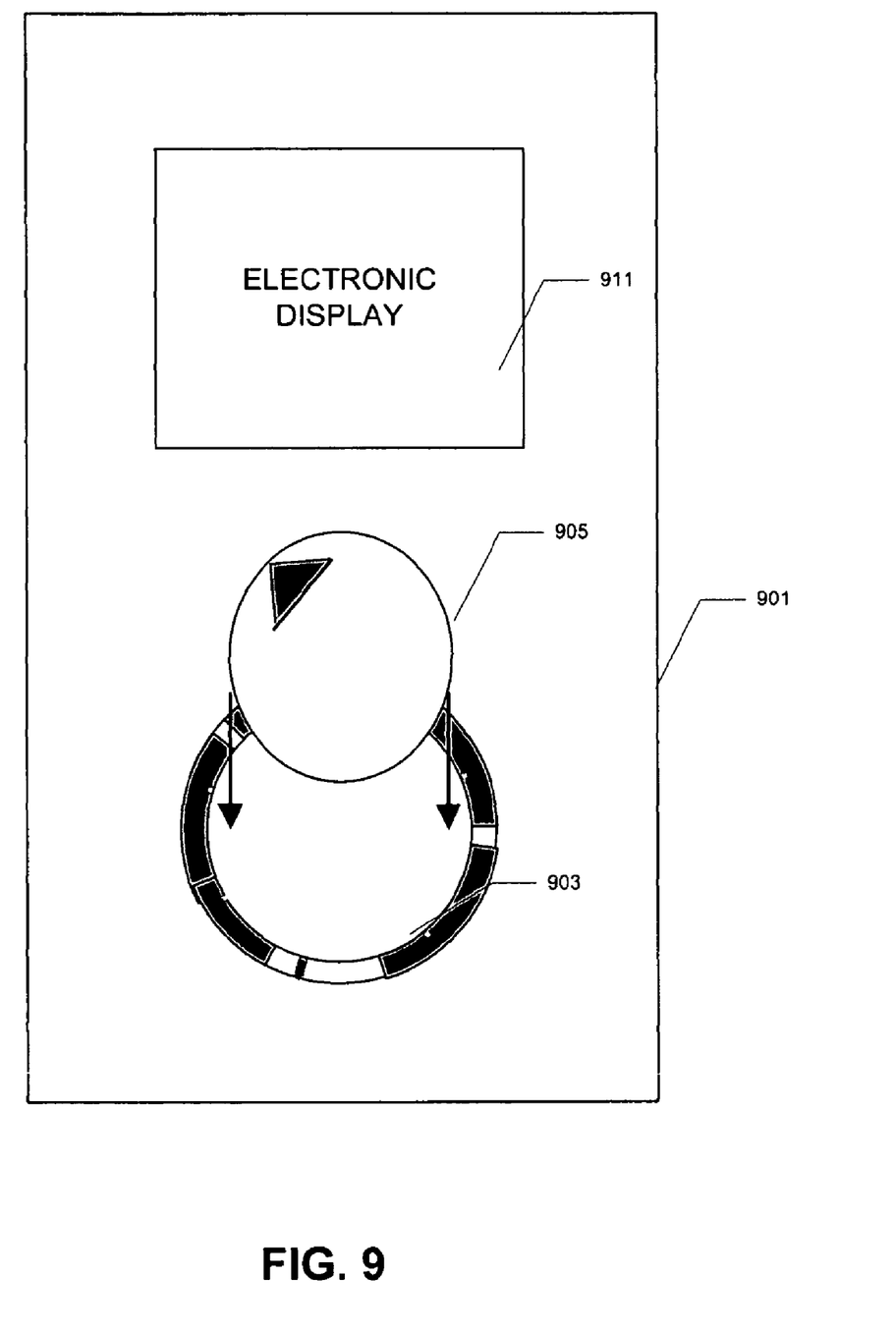
FIG. 9 illustrates a diagram of an improved electronic valve reader while used with an accompanying adjustment tool in accordance with an example embodiment of the present invention.

FIG. 9 illustrates a diagram of an improved electronic valve reader while used with an accompanying adjustment tool in accordance with an example embodiment of the present invention. In this embodiment, the reader 901 contains a display module 911 that displays the position of the valve once the reader 901 is positioned near an implanted flow control device. This process of determining the position of the valve is discussed above in detail.

Once the current position of the valve is determined and displayed, the adjustment tool 905 may be used to alter the setting for the valve within the flow control device. The adjustment tool corresponds to a magnetic coupling device that is placed over the valve reader sensor module 903 to orient the adjustment tool directly over the magnetic indication device that is part of the valve. The adjustment tool 905 magnetically couples to the magnetic indication device such that a rotation of the adjustment tool 905 within its location at above the valve reader sensor module 903 causes the magnetic indication device to rotate within the valve. This rotation of the magnetic indication device changes the settings for the valve within the flow control device as the magnetic indication device is directly coupled to the valve setting mechanism. The operation of the adjustment tool 905 is disclosed in additional detail with the published U.S. Patent application to Bertrand et al., No. 2002/0022873 as identified above. These modules operate together as disclosed herein to provide the operation of an electronic valve reader and valve adjustment tool.

Figure 10:
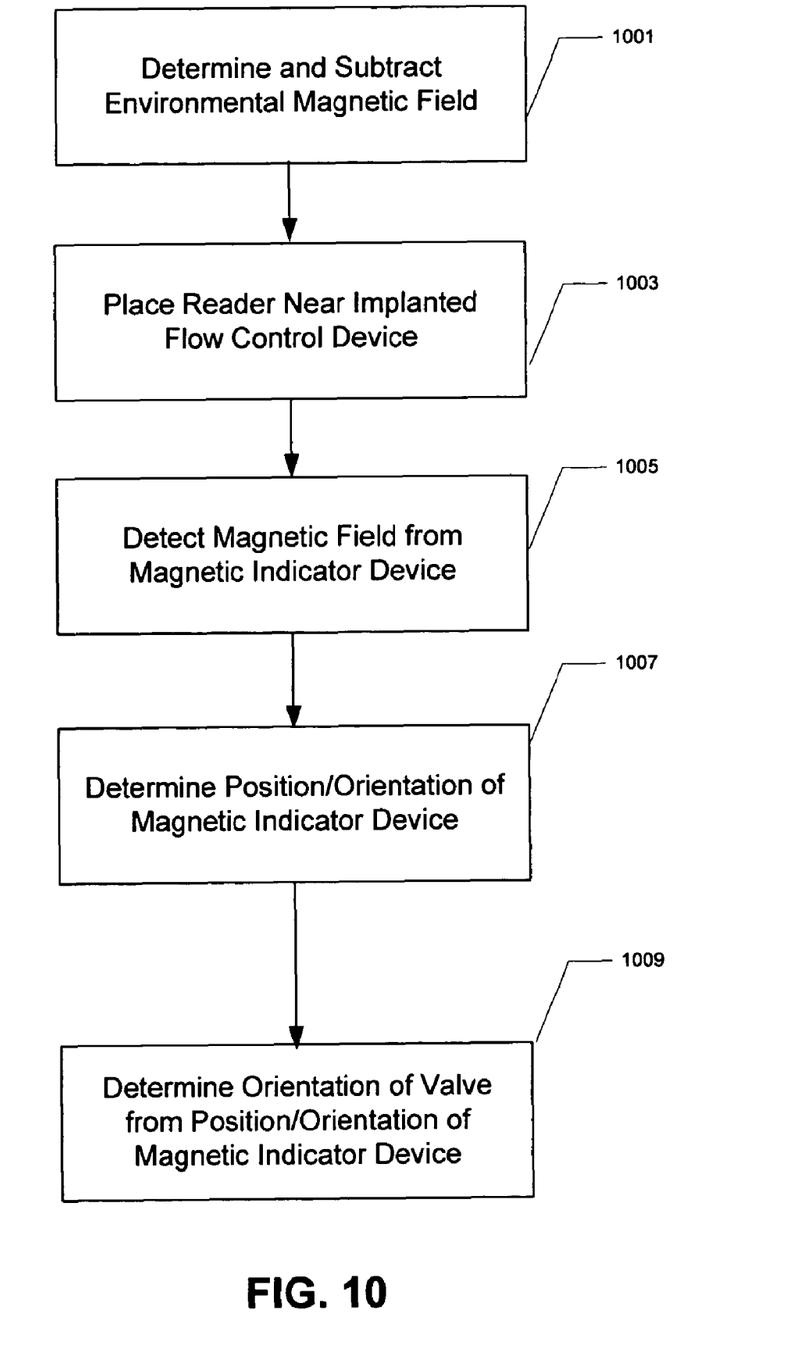
FIG. 10 illustrates a flowchart of a method for use of an improved electronic valve reader and adjustment tool in accordance with an example embodiment of the present invention.

FIG. 10 illustrates a flowchart of a method for use of an improved electronic valve reader and adjustment tool in accordance with an example embodiment of the present invention. The method for determining the setting of a valve within an implantable flow control device begins by determining an estimate for background magnetic fields 1001. This value is determined by obtaining a set of magnetic field values that are averaged to obtain this estimate for the background fields from environmental and ambient sources. Next, the method continues by placing 1003 of the reader near the implantable flow control device within a patient. Because the magnetic field typically observable at a distance of 12 cm from a typical magnetic indicator device coupled to an implantable flow control device is generally less than 5 milliGauss, the reader must be placed as close as possible to the flow control device to permit the reader to detect this magnetic field within the Earth's background magnetic field typically observed to be approximately 500 milliGauss.

Once the reader is located as close to the flow control device as possible, the reader detects an observed magnetic field 1005 from all sources. The background magnetic fields estimate 1001 is subtracted from the observed values 1005 to obtain a position and orientation for the magnetic indicator device 1007 coupled to the valve that is part of the implanted flow control device. The detected magnetic field measurements and processed position and orientation for the magnetic indicator device are repeated at a rate of several times per second.

The orientation of the magnetic indicator device is compared to a known orientation of the flow control device to determine a setting 1009 for the valve of the flow control device. The known orientation of the flow control device may be manually determined by requiring the reader to be oriented to a particular position relative to flow control device. The known orientation of the flow control device may also be determined from a detection of other reference positions, such as a separate reference magnet as discussed above. Once the reader has determined the setting for the valve, a user may utilize an adjustment tool to magnetically rotate and thus alter the setting of the valve as desired.

In the claims, any means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

Although the present invention has been described with reference to preferred embodiments, workers skilled in the art will recognize that changes can be made in form and detail without departing from the spirit and scope of the present invention.

What is claimed is:

1. An electronic magnetic-based indicator tool comprising:
   a housing having a display;
   a plurality of magnetic field sensors mounted with respect to the housing, wherein the plurality of magnetic field sensors determine spatial location and orientation of a magnetic indicator device associated with a valve on an implantable flow control device and a reference magnet coupled to the implantable flow control device at a location separate from the magnetic indicator device; and
   a processing module that receives magnetic data values from the plurality of magnetic field sensors and determines a setting for the valve using the determined orientation of the magnetic indicator device.

2. The electronic magnetic-base indicator tool of claim 1, wherein the processing module generates a display image corresponding to an orientation of the valve relative to the implantable flow control device and outputs the display image on the electronic display.

3. The electronic magnetic-base indicator tool of claim 1, wherein the processing module determines an estimate for ambient magnetic fields from a sequence of magnetic data values from the plurality of magnetic field sensors.

4. The electronic magnetic-base indicator tool of claim 3, wherein the processing module further subtract the estimate for ambient magnetic fields from received magnetic data values to determine the setting of the valve on the implantable flow control device.

5. The electronic magnetic-base indicator tool of claim 1, wherein the plurality of magnetic field sensors comprises four sets of three sensors for determining location and orientation of the magnetic indicator device in five degrees of freedom.

6. The electronic magnetic-base indicator tool of claim 5, wherein each of the four sets of three sensors being located about a respective one of four corners of the indicator tool.

7. The electronic magnetic-base indicator tool of claim 1, wherein the indicator tool further comprises an adjustment tool that modifies an orientation of the valve in the implantable flow control device.

8. The electronic magnetic-base indicator tool of claim 7, wherein the adjustment tool comprises a magnetic adjustment component that magnetically couples to the magnetic indicator device.

9. A system comprising
an implantable medical comprising a magnetic indicator device and a reference magnet, wherein the magnetic indicator device is associated with a valve on the implantable medical device and wherein the reference magnet is at a location separate from the magnetic indicator device;
an electronic magnetic-based indicator tool comprising:
a housing having a display;
a plurality of magnetic field sensors; and
a processing module that receives magnetic data values from the plurality of magnetic field sensors, determines and orientation of the indicator tool with respect to the magnetic indicator device and determines a setting for the valve; and
an adjustment tool that modifies an orientation of the valve, wherein the adjustment tool comprises a magnetic component for magnetically coupling to the magnetic indicator device.

10. The system of claim 9, wherein the processing module generates a display image corresponding to an orientation of the valve relative to the implantable flow control device and outputs the display image on the electronic display.

11. The system of claim 9, wherein the processing module determines an estimate for ambient magnetic fields from a sequence of magnetic data values from the plurality of magnetic field sensors.

12. The system of claim 11, wherein the processing module further subtract the estimate for ambient magnetic fields from received magnetic data values to determine the setting of the valve on the implantable flow control device.

13. The system of claim 9, wherein the plurality of magnetic field sensors comprises four sets of three sensors for determining location and orientation of the magnetic indicator device in five degrees of freedom.

14. The system of claim 13, wherein each of the four sets of three sensors being located about a respective one of four corners of the indicator tool.

15. The system of claim 9, wherein the indicator tool further comprises an adjustment tool that modifies an orientation of the valve in the implantable flow control device.

16. The system of claim 15, wherein the adjustment tool comprises a magnetic adjustment component that magnetically couples to the magnetic indicator device.

17. A method comprising
providing an implantable medical device having a magnetic indicator device and a reference magnet, wherein the magnetic indicator device is associated with a valve on the implantable medical device, and wherein the reference magnet is at a location separate from the magnetic indicator device;
placing an electronic magnetic-based indicator tool adjacent to the implantable medical device;
measuring a magnetic field with the indicator tool;
determining a spatial location and orientation of the implantable medical device using the measured magnetic field; and
determining an orientation of the valve using the measured magnetic field.

18. The method of claim 17, wherein the known position of the implantable medical device is determined from an expected orientation of the indicator tool relative to the implantable medical device.

19. The method of claim 17, wherein the known position of the implantable medical device is determined from determining a location and orientation of a reference magnetic device coupled to the implantable medical device.

20. The method of claim 17, wherein the measuring the magnetic field comprises:
receiving electronic signals from a plurality of magnetic field sensors, wherein the magnetic field sensors are grouped into a plurality of sets of three sensors located at separate locations within the indicator tool; and
processing the received electronic signals to determine an orientation and location of a magnetic device.

21. The method of claim 20, wherein the plurality of sets of three sensors comprises four sets of sensors, wherein each of the four sets of sensors is located about a respective one of four corners of the indicator tool.

* * * * *